United States Patent
Yamaguchi et al.

(10) Patent No.: US 8,118,881 B2
(45) Date of Patent: Feb. 21, 2012

(54) HAIR DYE AND HAIR DYE COMPOSITION

(75) Inventors: Masahiko Yamaguchi, Yokohama (JP); Shiro Irisa, Yokohama (JP); Eiji Takahashi, Yokohama (JP); Katsumasa Kikkawa, Yokohama (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 192 days.

(21) Appl. No.: 12/672,234

(22) PCT Filed: Sep. 25, 2008

(86) PCT No.: PCT/JP2008/067318
§ 371 (c)(1),
(2), (4) Date: Feb. 4, 2010

(87) PCT Pub. No.: WO2009/041514
PCT Pub. Date: Apr. 2, 2009

(65) Prior Publication Data
US 2011/0271465 A1    Nov. 10, 2011

(30) Foreign Application Priority Data

Sep. 26, 2007  (JP) .................................. 2007-249854
Mar. 31, 2008  (WO) .................. PCT/JP2008/056407

(51) Int. Cl.
*A61Q 5/10* (2006.01)
*C07C 50/18* (2006.01)
(52) U.S. Cl. .......... 8/405; 8/406; 8/423; 8/643; 552/208
(58) Field of Classification Search ............. 8/405, 406, 8/423, 643; 552/208
See application file for complete search history.

(56) References Cited

U.S. PATENT DOCUMENTS

| | | | |
|---|---|---|---|
| 4,367,334 A | 1/1983 | Loew | |
| 4,880,769 A | 11/1989 | Dix et al. | |

FOREIGN PATENT DOCUMENTS

| | | | |
|---|---|---|---|
| JP | 57-133158 A | 8/1982 |
| JP | 63-173692 A | 7/1988 |
| JP | 2-311566 A | 12/1990 |
| JP | 8-507545 A | 8/1996 |
| JP | 2003-246715 A | 9/2003 |

(Continued)

OTHER PUBLICATIONS

STIC Search Report dated Oct. 6, 2011.*

*Primary Examiner* — Eisa Elhilo
(74) *Attorney, Agent, or Firm* — Sughrue Mion, PLLC

(57) ABSTRACT

A hair dye containing a compound represented by the following general formula (I):

[Chemical Formula 1]

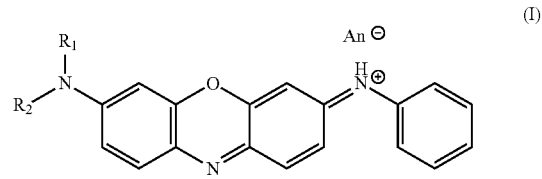

wherein $R_1$ and $R_2$ each independently represent a hydrogen atom or a straight chain or branched alkyl group having 1 to 5 carbon atoms, and $An^-$ represents an inorganic anion, an organic anion, or a complex salt anion, respectively.

14 Claims, 1 Drawing Sheet

FOREIGN PATENT DOCUMENTS

| | | |
|---|---|---|
| JP | 2004-035493 A | 2/2004 |
| JP | 2004-285048 A | 10/2004 |
| JP | 2005-179225 A | 7/2005 |
| JP | 2006-182727 A | 7/2006 |
| JP | 2007-022927 A | 2/2007 |
| JP | 2007-217321 A | 8/2007 |

* cited by examiner

HAIR DYE AND HAIR DYE COMPOSITION

TECHNICAL FIELD

The present invention relates to a hair dye and a hair dyeing composition. More particularly, the present invention relates to a hair dye and a hair dyeing composition comprising a cationic dye, which is suitable for dyeing keratin fibers contained in human hair and livestock hair.

BACKGROUND ART

Types of hair dyeing are, in general, roughly classified into the chemical reaction type (oxidative hair colorants) in which an oxidative dye such as paraphenylenediamine is mixed with a hydrogen peroxide solution at the time of use, thereby causing discoloration of melanin pigments in hair and oxidation color development so as to chemically react with a keratin fiber contained in the human hair, and the physical adsorption type (hair colorants) in which a direct dye such as an acidic dye and a basic dye physically adsorbs to a keratin fiber having positive or negative charge, thereby dye molecules penetrating into the hair to be dyed.

Most of hair dyeing is performed by a dyeing method using an oxidative dye, in which a colorless precursor substance is given to hair and this precursor substance is oxidation-polymerized to form a massive coloring substance. With this method, although hair dye can be maintained stably over a long period of time, a part of diamine based oxidative dyes may cause a skin allergy reaction (skin roughness) in rare cases depending on constitutions. Further, since an alkaline agent such as ammonium is contained as other components, there is a defect such as damaging of hair.

On the other hand, typical products for temporally coloring hair include a hair manicure and a color conditioner, and a main dye of these hair manicure and color conditioner is an acidic dye used in cosmetics. Since the acidic dye has low allergic reactivity as compared with the above described oxidative dye, and there is thus an advantage such as being usable for persons in whom skin roughness is caused by an oxidative hair colorant. Further, since an alkaline agent is not used, less damage to hair is caused. However, as compared with a chemical reaction type oxidative dye, there is a defect such that color fading is likely to occur at the time of washing hair.

As the colorant for temporally coloring hair such as hair manicure, basic dyes and the like are used in addition to oxidative dyes, and fastness of hair dyeing by these basic dyes is around at a middle degree. In particular, among basic dyes, color fastness to light and shampoo fastness of hair dyeing by a cationic dye are said to be low.

A dye can be formed into any color prepared by suitably blending the three primary colors of the dye in combination. In particular, in the case of a reaction type oxidative hair colorant, a mixing ratio with an oxidant is changed for each color number, so a color in hair dyeing is different from the color number in many cases. On the other hand, since each dye developing a color is used in blending in the case of a hair colorant such as a hair manicure, the hair colorant has an advantage such as easily preparing into a desired color number.

Among the three primary colors of a dye used in a hair manicure and color conditioners, blue base is an essential blending color for brown base and black base, which are basic blending colors for dyeing hair. Further, a blue dye accounts for a comparatively larger blending in terms of an amount to be used, while only a few is excellent in dyeing properties, color tone and fastness, and color at the time of fading, unevenness in dyeing, and the like give large effects on quality of a hair dyeing composition that is a product.

As a method of rapidly dyeing a keratin fiber of human hair or livestock with the above descried direct dye, there are documents relating to a method of dyeing by using an arylmethane dye, a cationic azo dye, a methine dye, an azomethine dye, and the like in a suitable solvent for dyeing (for example, see Japanese Patent Application Laid-Open No. 2004-285048) and a method of dyeing a keratin-containing fiber, particularly human hair, with a cationic dye (for example, see Japanese Published Patent Publication No. 8-507545).

In particular, since a cationic dye has high dyeing properties and preferable water solubility, the cationic dye is suitable for dyeing human hair and livestock hair, but color fastness to light and shampoo fastness of hair dyeing have not been sufficient yet.

[Patent document 1] Japanese Unexamined Patent Application Publication No. 2004-285048
[Patent document 2] Japanese Unexamined Patent Application Publication (Translation of PCT Application) No. 8-507545

DISCLOSURE OF THE INVENTION

Problems to be Solved by the Invention

An object of the present invention is to provide a hair dye excellent in color fastness to light, dyeing properties, and shampoo fastness, and a hair dyeing composition containing the same.

Means for Solving the Problems

The present invention provides a hair dye containing a compound represented by the following general formula (I):

[Chemical Formula 1]

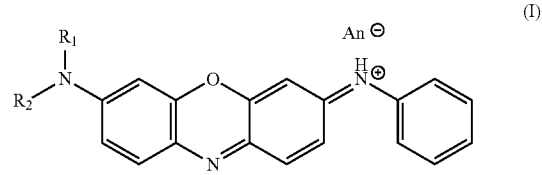

wherein $R_1$ and $R_2$ each independently represent a hydrogen atom or a straight chain or branched alkyl group having 1 to 5 carbon atoms, and $An^-$ represents an inorganic anion, an organic anion, or a complex salt anion, respectively.

The hair dye containing a compound represented by the general formula (I) belongs to a blue cationic dye, and the present inventors found that this compound is extremely excellent in dyeing properties of keratin fibers contained in human hair, livestock hair, etc., and also favorable in color fastness to light and shampoo fastness. The hair dye containing a compound represented by the above described general formula (I) has an advantage of allowing direct dyeing from an aqueous dye solution at room temperature without using any auxiliary agent. Further, the chemical formula represented by the general formula (I) can be also expressed by a resonance structure represented by the following general formula (I') (hereinafter, description of the resonance structure for a compound having the same skeleton as the general formula (I) is omitted).

[Chemical Formula 2]

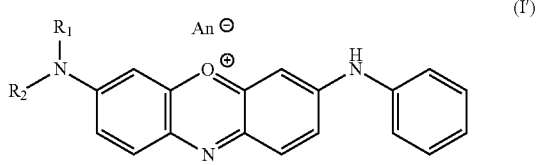

Examples of the inorganic anion in the general formula (I) include a chlorine ion, a bromine ion, a sulfate ion, a phosphate ion, or an iodine ion, and examples of the complex salt anion include an inorganic complex salt anion represented by the following general formula (II):

wherein n represents a number of 0.5 to 1.

It is preferable that both of $R_1$ and $R_2$ in the general formula (I) are an ethyl group or an n-butyl group.

A compound in which both $R_1$ and $R_2$ are an ethyl group is a dye known as C. I. Basic Blue 75 (CAS. No. 12221-43-1, CAS No. 73398-25-1). It has been known that this dye can dye an acrylic fiber that is a synthesis fiber by bonding a sulfonic acid group, however, keratin fibers such as human hair and animal hair are composed of protein and the dyeing mechanism is completely different, thus it has not been known at all that such a fiber can be dyed, and a use as a hair dye was found at first time by the present inventors. Further, the hair dye containing C. I. Basic Blue 75 has extremely high dyeing concentration for hair as compared with conventional basic blue dyes, and is also exceptionally excellent in color fastness to light and shampoo fastness of a dyed product, and extremely useful as a blue hair dye.

A compound in which both $R_1$ and $R_2$ are an n-butyl group in the general formula (I) is a novel chemical substance firstly synthesized by the inventors in this time, and as compared with conventional basic blue dyes, the compound is exceptionally excellent in dyeing (dyeing concentration) of a keratin fiber of human hair, animal hair, and the like, and useful as a hair dye extremely favorable in color fastness to light and shampoo fastness.

The present invention also provides a hair dyeing composition containing the hair dye comprising a compound represented by the above general formula (I), at least one auxiliary agent selected from the group consisting of a wetting agent, a swelling agent, a penetrant, a pH regulator, a surfactant, a perfume and a thickener, and water.

Such a hair dyeing composition can be used as a so-called hair colorant, and exerts favorable dyeing properties, color fastness to light and shampoo fastness.

The hair dyeing composition can further contain an oxidative dye, an alkaline agent, and an oxidant.

Such a hair dyeing composition can be used as a so-called oxidative hair colorant, and is not only excellent in dyeing properties, color fastness to light and shampoo fastness, but also has characteristics such that stability is excellent in the state of coexistence with an alkaline agent and an oxidant.

In the hair dyeing composition, from the viewpoint of dyeing properties, a content of a hair dye is preferably 0.001 to 5% by mass on the basis of the total amount, and a pH is preferably 3 to 10.

Further, a surfactant contained in the hair dyeing composition is suitably a polyoxyethylene sorbitan fatty acid ester. Use of such a surfactant together with a compound represented by the general formula (I) enables reduction in skin contamination.

From the viewpoint of an effect of reducing contamination to the skin, it is preferable that the polyoxyethylene sorbitan fatty acid ester is at least one selected from the group consisting of polyoxyethylene sorbitan monolaurate, polyoxyethylene sorbitan monopalmitate, polyoxyethylene sorbitan monostearate, and polyoxyethylene sorbitan monooleate. A content of the polyoxyethylene sorbitan fatty acid ester is preferably 2.5 to 30 fold more than the amount of a hair dye on the mass basis.

The hair dyeing composition is applicable, for example, as a liquid hair dyeing composition, a gel type hair dyeing composition, a cream type hair dyeing composition, and a foam type hair dyeing composition.

The present invention also provides a compound represented by the following general formula (Ia):

[Chemical Formula 3]

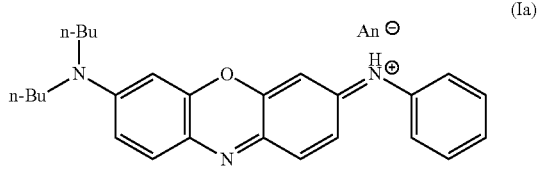

wherein $An^-$ represents an inorganic anion, an organic anion, or a complex salt anion, and n-Bu represents an n-butyl group.

The compound represented by the above general formula (Ia) is a novel chemical substance and is useful as a hair dye compound. In the general formula (Ia), the inorganic anion is preferably a chlorine ion, a bromine ion, a sulfate ion, a phosphate ion, or an iodine ion, and the complex salt anion is preferably an inorganic complex salt anion represented by the following general formula (II):

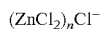

In the formula, n represents a number of 0.5 to 1.

Effect of the Invention

According to the present invention, utilizing high dyeing properties and preferable water soluble characteristics of a cationic dye comprising a compound represented by the general formula (I), a blue hair dye and a hair dyeing composition (hair colorant composition, oxidative hair colorant composition, etc.) which are suitable for dyeing keratin fibers contained in human hair, livestock hair and the like are provided.

Further, as apparent from the evaluation test results of hair dyeing, the hair dye and the hair dyeing composition of the present invention are also improved in color fastness to light as compared with cationic dyes that are conventional hair dyes. Furthermore, the hair dye and the hair dyeing composition are also excellent in shampoo fastness, and can suppress unnatural color at the time of fading.

The hair dyeing composition of the present invention can be used in a wide range of pH value from 3 to 10, and a brown dye and a red dye are blended in a hair dye comprising a compound represented by the general formula (I), thereby forming into a black dye preparation. Further, blending a brown dye enables to form into a brown dye preparation.

BEST MODE FOR CARRYING OUT THE INVENTION

Figure 1:
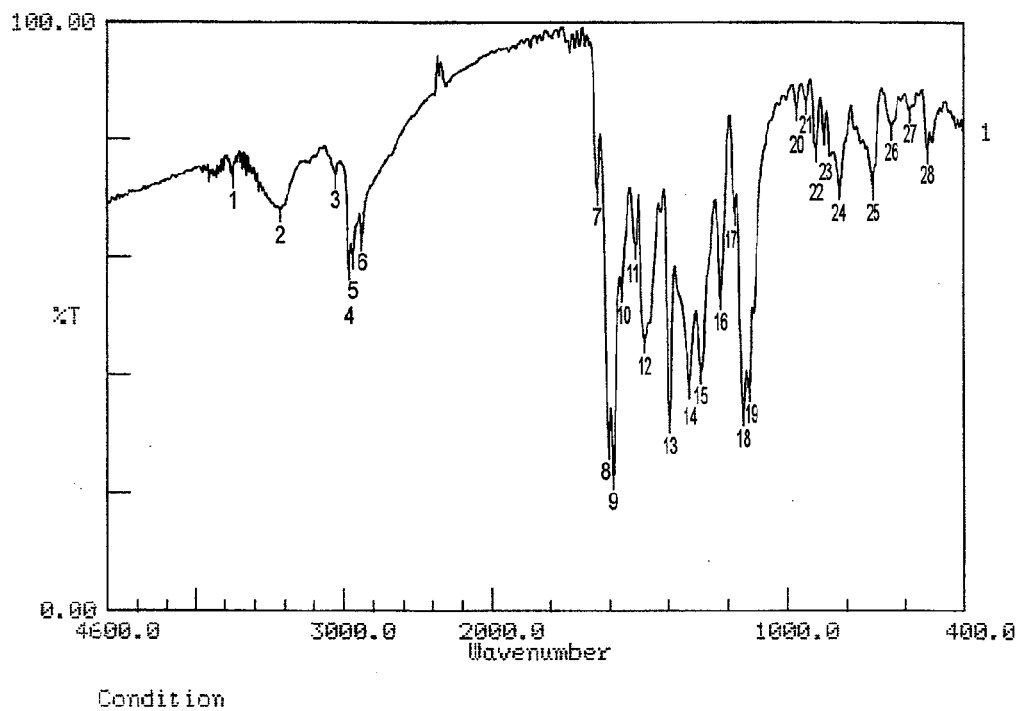
FIG. 1 shows an infrared absorption spectrum of the compound obtained in Example 1-1.

Hereinafter, embodiments of the present invention will be specifically explained.

The hair dye of the present invention contains a compound represented by the above described general formula (I), and is a blue dye classified into an oxazine dye.

[Chemical Formula 4]

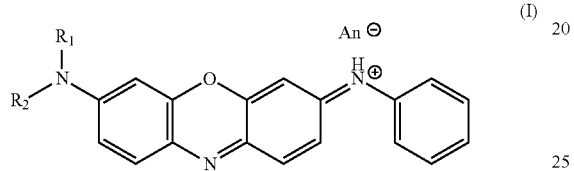
(I)

The compound represented by the general formula (I) can be synthesized by, for example, the scheme shown in the following.

First, diphenylamine represented by the following formula (I) is nitrosated by adding a sodium nitrite, and the like under acidic conditions. Thereby, an N-nitroso compound represented by the following formula (II) is obtained, and a p-nitroso compound represented by the following formula (Iii) is obtained by Fischer-Hepp transfer.

[Chemical Formula 5]

Then, the compound represented by the formula (iii) is reacted with aminophenol represented by the general formula (iv) under acidic conditions, thereby forming an oxazine ring to obtain a compound represented by the general formula (I'). The compound represented by the general formula (I') can be also expressed by the compound of the general formula (I) by resonance, and any of these compounds constitute the hair dye of the present invention.

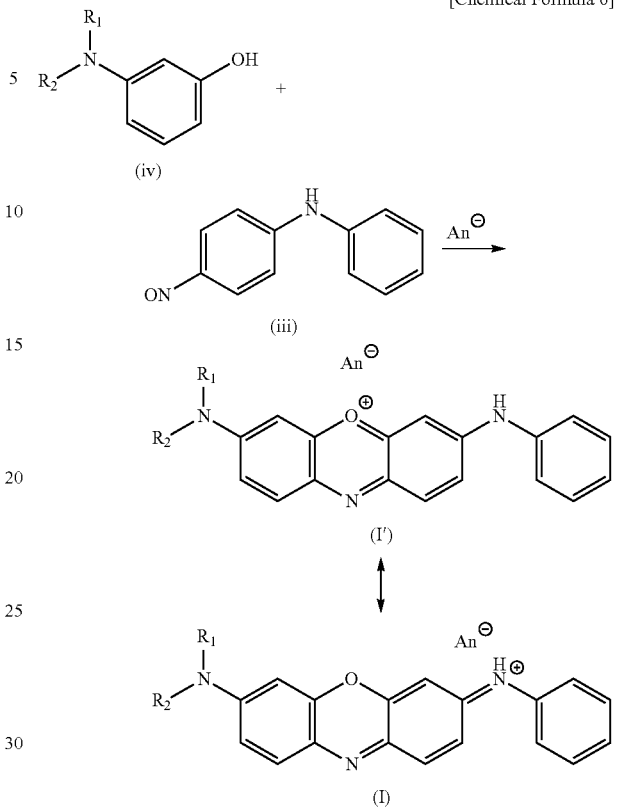

[Chemical Formula 6]

In the general formula (I), $R_1$ and $R_2$ each independently represent a hydrogen atom or a straight chain or branched alkyl group having 1 to 5 carbon atoms. The alkyl group is preferably a straight chain or branched alkyl group having 1 to 4 carbon atoms, and more preferably a straight chain alkyl group having 1 to 4 carbon atoms (methyl group, ethyl group, n-propyl group, n-butyl group). $R_1$ and $R_2$ may be the same or different.

In the general formula (I), $An^-$ indicates an inorganic anion, an organic anion, or a complex salt anion. The complex salt anion is preferably an inorganic complex salt anion.

Example of the organic anion include an acetate ion, an oxalate ion, methanesulfonate ion, a trifluoromehanesulfonate ion, a 4-toluenesulfonate ion, and a benzenesulfonate ion, and these ions can be introduced by adding acetic acid, oxalic acid, methanesulfonic acid, trifluoromethanesulfonic acid, 4-toluenesulfonic acid, and benzenesulfonic acid, respectively, during or after forming an oxazine ring shown in the above described reaction scheme.

$An^-$ is preferably an inorganic anion or a complex salt anion, and examples of the inorganic anion include a chlorine ion, a bromine ion, a sulfate ion, a phosphate ion, and an iodine ion. Among these ions, a chlorine ion is suitable. In addition, a chlorine ion, a bromine ion, a sulfate ion, a phosphate ion, and an iodine ion can be introduced by adding hydrochloric acid, hydrobromic acid, sulfuric acid, phosphoric acid, hydroiodic acid, respectively, during or after forming an oxazine ring shown in the above described reaction scheme.

As a complex salt anion, an inorganic complex salt anion represented by the following general formula (II) is particularly preferable. In the general formula (II), n represents a number of 0.5 to 1. The inorganic complex salt anion represented by the following general formula (II) can be introduced by adding hydrochloric acid and zinc chloride during or after forming an oxazine ring shown in the above described reaction scheme.

$(ZnCl_2)_n Cl^-$           (II)

Regarding a compound in which both $R_1$ and $R_2$ are an ethyl group among compounds represented by the general formula (I), a desired product can be obtained as a preferable crystal by even using only water as a reaction solvent. On the other hand, regarding a compound in which both $R_1$ and $R_2$ are an n-butyl group, if a reaction medium is only water, a desired product is formed into a harz state, thereby extremely reducing a yield. However, the present inventors found that use of a reaction solvent obtained by adding an alcohol to water enables to obtain a powdery desired product with a high yield.

The first embodiment of the hair dyeing composition of the present invention is a form as, what is called, a hair colorant, and contains the hair dye comprising a compound represented by the general formula (I), at least one auxiliary agent selected from the group consisting of a wetting agent, a swelling agent, a penetrant, a pH regulator, a surfactant, a perfume and a thickener, and water.

Examples of the wetting agent include glycerin, propylene glycol, sorbitols, 1,3-butylene glycol, polyethylene glycols. Examples of the swelling agent include aqueous alkaline solutions containing ammonia (ammonia hydroxide) or monoethanolamine (MEA).

Examples of the penetrant include monohydric alcohols having an alkyl group with 1 to 6 carbon atoms such as ethanol, 1-propanol, 2-propanol, 1-butanol, and 2-butanol; polyhydric alcohols having 3 to 8 carbon atoms such as propanediol, butanediol, pentanediol, hexanediol, hexanetriol, heptanediol, heptanetrial, octanediol, octanetriol, isoprene glycol, propylene glycol, glycerin, and diethylene glycol monoethyl ether, or esters thereof; N-alkylpyrrolidone being liquid at normal temperature such as N-methyl-2-pyrrolidone, N-ethyl-2-pyrrolidone, N-propyl-2-pyrrolidone, N-butyl-2-pyrrolidone, and N-cyclohexyl-2-pyrrolidone; alkylene carbonate (lower alkylene carbonate) such as ethylene carbonate and propylene carbonate; aromatic alcohols such as benzyl alcohol, benzyloxyethanol, cinnamyl alcohol, p-anisyl alcohol, p-methylbenzyl alcohol, phenoxyethanol, phenoxyisopropanol, 2-benzyl ethanol, and β-phenylethyl alcohol. Among these examples, aromatic alcohols, lower alkylene carbonate, N-alkylpyrrolidone are preferable, and in particular, benzyl alcohol, benzyloxyethanol, and propylene carbonate are preferable. Examples of the pH adjuster include acids such as phosphoric acid, lactic acid-sodium lactate, and citric acid-sodium citrate, alkalis such as ammonium water, sodium hydroxide, potassium hydroxide, and sodium carbonate.

Examples of the surfactant include sugar alcohol ethers such as a polyoxyethylene alkyl ether, a polyoxyethylene fatty acid ester, a polyglycerin fatty acid ester and a sorbitol alkyl ether, and a polyoxyethylene sorbitan fatty acid ester.

Among them, polyoxyethylene sorbitan fatty acid ester is particularly preferable. By using a polyoxyethylene sorbitan fatty acid ester, the effect of reducing contamination to the skin becomes excellent.

The polyoxyethylene sorbitan fatty acid ester is preferably least one selected from the group consisting of polyoxyethylene sorbitan monolaurate, polyoxyethylene sorbitan monopalmitate, polyoxyethylene sorbitan monostearate, and polyoxyethylene sorbitan monooleate.

From the viewpoint of reduction in contamination to the skin, a content of a polyoxyethylene sorbitan fatty acid ester is preferably 2.5 to 30 fold more than the amount, more preferably 10 to 20 fold more than the amount of a hair dye comprising a compound represented by the general formula (I) on the mass basis.

The polyoxyethylene sorbitan fatty acid ester is particularly excellent in protection performance of skin contamination when combined with the hair dye comprising a compound represented by the general formula (I).

Examples of the perfume in the hair dyeing composition include vanillin, cinnamic alcohol, heliotropine, coumalin, 2-methyl-3-(3,4-methylenedioxy-phenyl)-propanal, 4-(4-hydroxyphenyl)-2-butanone, benzaldehyde, anisyl alcohol, 3,4-dimethoxybenzaldehyde, heliotropyl acetate, phenyl acetaldehyde dimethylacetal, phenoxyethyl alcohol, phenyl acetaldehyde glycerylacetal, benzyl alcohol, phenylethyl alcohol, Franeol, sugar lactone, manthol, ethyl manthol, ethyl diglycol, benzyl acetate, linalool, camphor, terpineol, citronellol, geraniol, 2,6-nonadienol, methyloctyl carbonate, 3,7-dimethyl-2,6-octadienal, and nonanal. Examples of a thickener include xanthan gum, collagen, gelatin, carboxymethylcellulose sodium salt, Carbopol (registered trademark), sodium alginate, gum Arabic, cellulose derivatives, and thickeners derived from poly(ethylene oxide).

In the first embodiment of the hair dyeing composition (hair colorant), the composition preferably contains a hair dye comprising a compound represented by the general formula (I) in an amount of 0.001 to 5% (more preferably 0.01 to 5% by mass, and further more preferably 0.05 to 2% by mass), by mass based on the total amount of the hair dyeing composition, with balance being at least one auxiliary agent selected from the group consisting of a wetting agent, a swelling agent, a penetrant, a pH regulator, a surfactant, a perfume and a thickener, and water.

In the second embodiment of the hair dyeing composition of the present invention is in a form of, so-called, oxidative hair colorant, the composition contains a hair dye comprising a compound represented by the general formula (I), at least one auxiliary agent selected from the group consisting of a wetting agent, a swelling agent, a penetrant, a pH regulator, a surfactant, a perfume and a thickener, water, an oxidative dye, an alkaline agent, and an oxidant.

In the second embodiment, preferable examples of the wetting agent, swelling agent, penetrant, pH regulator, surfactant, perfume and thickener are the same as in the first embodiment.

In the second embodiment, examples of the oxidative dye include paraminophenol, paraphenylenediamine, resorcin, and catechol. Examples of the alkaline agent include ammonia water; alkylamine such as monoethylamine, diethylamine, and triethylamine; alkanolamine such as triethanolamine and monoethanolamine; sodium hydroxide, potassium hydroxide, and sodium carbonate. Examples of the oxidant include a hydrogen peroxide solution, sodium perborate, and urea peroxide.

Water used in the second embodiment is blended in order to dissolve the hair dye represented by the general formula (I) and auxiliary agents, and ion-exchanged water, purified water, and clarified water can be applied. In addition, the same water as in the second embodiment can be used for the same purpose also in the first embodiment.

In the second embodiment of the hair dyeing composition (oxidative hair colorant), the composition preferably contains a hair dye comprising a compound represented by the general formula (I) in an amount of 0.001 to 5% by mass based on the total amount of the hair dyeing composition, with balance being an auxiliary agent, water, an oxidative dye, an alkaline agent, and an oxidant. In addition, the hair dye comprising a compound represented by the general formula (I) shows clean blue color that is not shown in an oxidative dye, and blending in the oxidative dye enables color variation (color phase range) to become broad.

When the content of the hair dye is less than 0.001% by mass, the effects of keeping color tone and dyeing uniformity are hardly obtained, and when the hair dye is added in an amount exceeding 5% by mass, the effects such as dyeing and the like are also less improved. The content of the hair dye is preferably 0.01 to 5% by mass, and more preferably 0.05 to 2% by mass based on the total amount of the hair dyeing composition.

To the hair dyeing composition of the present invention, conventionally known cosmetic components can be also added and used within the range where the effects of the present invention are not inhibited. As components that can be added, examples thereof include a higher alcohol, Vaseline, a polyvalent alcohol, esters, an antiseptic agent, a bactericide, a silicone derivative, and a thickener. The pH value of the hair dyeing composition is 3 to 10, and preferably 4 to 9.

EXAMPLES

Hereinafter, the present invention will be more specifically described referring to Examples and Comparative Examples, but, the present invention is not limited to Examples below.

Example 1-1

52.8 g of 4-nitrosodiphenylamine (30% wet product) and 150 ml of water were added, thereto were added 17.4 g of N,N-di-n-butyl-m-aminophenol and 570 ml of ethanol, and the mixture was adjusted to pH 1.0 with 35% hydrochloric acid, then 0.9 g of magnesium oxide was added, and the mixture was reacted at 60 to 80° C. for 5 hours while the pH was kept at 1.1 to 1.2 with sodium acetate. Thereto were added 6.6 g of perlite and 1.9 g of active carbon, after stirring for 1 hour, the mixture was subjected to heat filtration to remove impurities, 420 g of hot water was added, 16.1 g of zinc chloride and 45.6 g of sodium chloride were added, and the reaction mixture was left at 20 to 40° C. for 10 hours, then a precipitated crystal was filtered off and dried. A hair dye having the following structure (hereinafter, referred to as a "dibutyl product") was obtained (yield of 28.8 g).

[Chemical Formula 7]

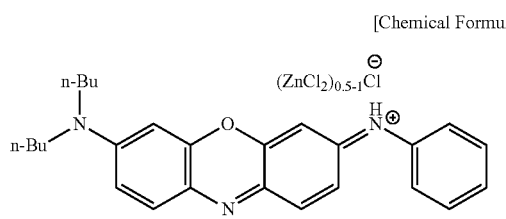

Example 1-2

217 g of diphenylamine was dissolved in 400 ml of water, 125 g of 95% sulfuric acid and 500 ml of xylene, and 243 g of 40% sodium nitrite and 80 ml of water were nitrosified at 30° C. After liquid separation, 125 g of diethyl-m-aminophenol, 8 g of magnesium hydroxide and 1600 ml of water were added while the aqueous layer were kept at 30° C. or less, and the mixture was adjusted to pH 1.2 with 40% sodium acetate. While keeping the pH at 1.1 to 1.2, the reaction was performed at 60 to 80° C. for 5 hours, and the remaining xylene was removed by steam distillation. Warm water was added to make an entire amount set to be 10 L and the pH was adjusted to 4 to 4.5 with sodium bicarbonate. The insoluble substance was filtered off with perlite and active carbon, 3.2 L of hot water was then added, and the mixture was adjusted to pH 2 with hydrochloric acid. Thereto were added 69 g of zinc chloride and 2730 g of saturated saline, the mixture was left at 20 to 40° C. for 10 hours, the precipitated crystal was filtered off and dried to obtain a hair dye having the following structure (hereinafter, referred to as "C. I. Basic Blue 75" or abbreviated as "Blue 75") (yield: 172 g).

[Chemical Formula 8]

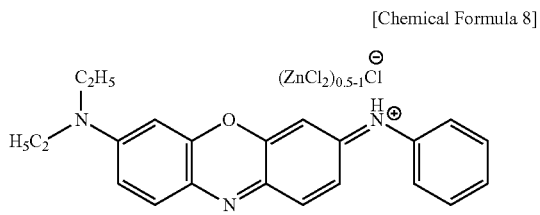

As a physicochemical characteristic value of the obtained dye compound, a maximum absorption wavelength (λmax) in a visible region of a dye solution is described in Table 1. The dibutyl product and Blue 75 are both cyan color, the dibutyl product has a higher wavelength by 5 nm as compared with Blue 75, which indicates brighter blue. By blending dyes with other colors for hair colors, the both compounds gave basic blue dyes, which can express various kinds of color phase ranges. Note that the test sample used in the measurement was prepared as follows. 0.100 g of the hair dye obtained in Examples 1-1 and 1-2 and 0.100 g of acetic acid (reagent special grade, made by Wako Pure Chemical Industries, Ltd.) were weighed, and diluted with distillation water at 80° C. until the volume reached 100 ml in total. This diluted solution was subjected to an ultrasonic treatment for 1 hour, then 1 ml thereof was weighted and diluted with distillation water having a room temperature until the volume reached 250 ml in total to thereby obtain a sample used in the measurement. In the measurement, a spectrophotometer UV-160A manufactured by SHIMADZU CORPORATION was used. A concentration of the λmax measured solution was $4.0 \times 10^{-6}$ g/ml.

TABLE 1

| Hair dye | Maximum absorption wavelength (nm) |
|---|---|
| Dibutyl product | 649.0 |
| Blue75 | 645.0 |

Using FT/IR-5300 manufactured by JASCO Corporation, an ultrared absorption spectrum of the dibutyl product was measured. The spectrum and absorption peak wavenumber are shown in FIG. 1. Note that the test sample used in the measurement was prepared as follows. The dibutyl product (hair dye) prepared in Example 1-1 and potassium bromide in an amount of 300 hold weight of the dibutyl product were kneaded well with a mortar, and then compressed with a hand-operated press machine to thereby obtain a sample used in the measurement.

Names of dyes described in Examples and Comparative Examples below are abbreviated as follows.
C. I. Basic Blue 75: Blue 75
C. I. Basic Blue 3: Blue 3
C. I. Basic Blue 99: Blue 99
C. I. Basic Brown 16: Brown 16
C. I. Basic Red 29: Red 29
C. I. Basic Red 51: Red 51

Example 2

(Hair Dyeing Method 1)

Dyeing solutions A, B and C prepared from Blue 75 obtained in Example 1-2 based on composition ratios in Table 2 were weighed in an amount of 10 g, respectively, and adjusted to pH 8.5 with monoethanolamine, then 1 g of artificial white hair (100%) (product No. BM-W, Beaulax Co., Ltd.) was placed therein and then dyed at 45° C. for 20 minutes. This dyed hair was washed with water, subjected to soaping under the soaping conditions described below and washed with water, and then dried at room temperature to thereby obtain test samples, respectively. Note that dye concentrations when 10 g of these dyeing solutions A, B and C used to dye 1 g of hair respectively correspond to 1%, 2% and 3% owh (*1).
(% owh (*1): indicates % by weight of a dye with respect to a mass of hair.)

TABLE 2

| | | Composition | | |
| | | Composition ratio (mass %) | | |
| Component | Component name | Dyeing solution A | Dyeing solution B | Dyeing solution C |
|---|---|---|---|---|
| (a) Component | Dye | 0.1 | 0.2 | 0.3 |
| (b) Component | Ethanol | 20 | 20 | 20 |
| | Benzyl alcohol | 9 | 9 | 9 |
| (c) Component | Water (ion exchange water) | 70.9 | 70.8 | 70.7 |
| Total amount: | — | 100 | 100 | 100 |

Further, water is blended in order to dissolve the dye (a) component and the auxiliary agent (b) component, and the composition ratio is a remnant obtained by deducting the mass % of the components (a) and (b) from the entire 100% by mass. As water, in addition to ion-exchanged water, purified water and clarified water can be also used.

The dyeing solutions A, B and C in Table 2 are dye solutions prepared from Blue 75 in hair dyeing compositions set at 0.1, 0.2 and 0.3% by mass, respectively.

Comparative Example 1

Blue 3 was selected as a dye subjected to a test, and test samples (dyeing solutions A to C) were obtained in accordance with the hair dyeing method 1 in Example 2. Blue 3 is the dye of the formula (8) described in Japanese Published Patent Publication No. 8-507545 and the dye of the formula (XIII) described in Japanese Patent Application Laid-Open No. 2004-285048, Paragraph [0016], which are the compounds having the same oxazine skeletons as Blue 75 and expressed by the following chemical formula:

[Chemical Formula 9]

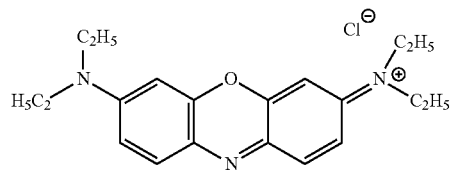

Comparative Example 2

Blue 99 was selected as a dye subjected to a test, and test samples (dyeing solutions A to C) were obtained in accordance with the hair dyeing method 1 in Example 2. Blue 99 is also referred to Arianor Steel Blue as another name, which is a standard dye used for blue hair dyeing, and a mixture of compounds represented by the following chemical formulas:

[Chemical Formula 10]

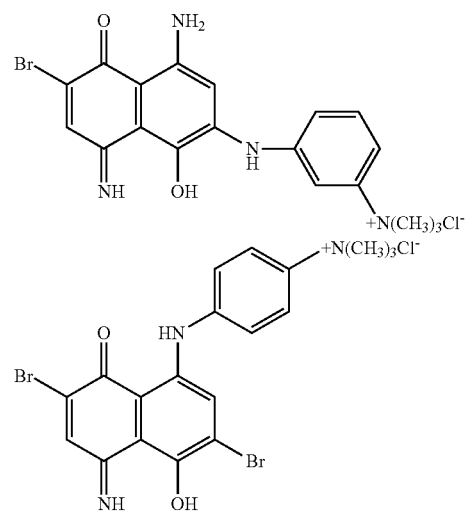

The soaping conditions are as follows.
<Soaping Conditions>
Soaping solution: 5% Tween #80 aqueous solution (polyoxyethylene sorbitan monooleate, made by Kanto Chemical Co., Inc.)
Bath ratio: 1:10 (mass of a soaping solution with respect to 1 g of dyeing hair mass)
Treatment temperature, time: 45° C., 10 minutes
After treatment: Washing with water A dyeing concentration of each test sample was measured. The measurement result thereof is described in Table 3. The measurement conditions are described in the following.

TABLE 3

| Dye concentration | | Dyeing concentration (K/Sd) (*2) | |
|---|---|---|---|
| % owh (*1) | Dye name | Test sample | Ratio (*3) |
| 1 | Blue75 | 258 | 100 |
| | Blue3 | 121 | (47) |
| | Blue99 | 78 | (30) |

TABLE 3-continued

| Dye concentration % owh (*1) | Dye name | Dyeing concentration (K/Sd) (*2) | |
|---|---|---|---|
| | | Test sample | Ratio (*3) |
| 2 | Blue75 | 472 | 100 |
| | Blue3 | 223 | (47) |
| | Blue99 | 130 | (28) |
| 3 | Blue75 | 563 | 100 |
| | Blue3 | 317 | (56) |
| | Blue99 | 203 | (36) |

(*1) % owh: shows mass % of a dye with respect to a mass of hair
(*2) K/Sd: value obtained by deducting K/S of undyed hair from K/S of hair dyeing test sample
(*3) ( ) value: dyeing concentration ratio of each dye when a dyeing concentration of Blue 75 is assumed to be 100

(Dyeing Concentration)
For a dyeing concentration of each hair, an optical concentration (K/Sd) was calculated from the following formula (Kubelka-Munk formula).

$$K/S_\lambda = \Sigma(1-R_\lambda)^2/2R_\lambda$$

$R_\lambda$: reflective ratio (%)/100
$\lambda$: 10 nm interval from 380 to 780 nm
The reflective ratio R measurement was measured with a spectrocolorimeter SE-2000 (manufactured by NIPPON DENSHOKU INDUSTRIES CO., LTD.).

From the measurement results of Table 3, regarding a dyeing concentration of hair at a pH value of 8.5, Blue 75 is higher in any dyeing concentration level as compared with Blue 3 that is the same oxazine blue dye and Blue 99 that is an arianor dye, and Blue 75 is obviously excellent in dyeing properties.

Example 3

On each test sample with a dyeing solution concentration of 3% owh obtained by the dyeing method 1, a test of color fastness to light was carried out in the following conditions, and dyeing concentrations were measured for each sample before and after the test. The measurement results are described in Table 4.
(Test of Color Fastness to Light)
Light resistant tester: Ultraviolet long life fade meter FAL-5H (manufactured by SUGA TEST INSTRUMENTS CO., LTD.)
Irradiation time: 10 Hr (hours), 20 Hr (hours)

TABLE 4

| Dye concentration % owh (*1) | Dye name | Irradiation time (fade meter) | | | Residual ratio (%) (20 Hr) (*4) |
|---|---|---|---|---|---|
| | | Unirradiated (K/Sd) | 10 Hr (K/Sd) | 20 Hr (K/Sd) | |
| 3 | Blue75 | 563 | 439 | 332 | 59 |
| | Blue3 | 317 | 123 | 91 | 29 |
| | Blue99 | 203 | 193 | 140 | 69 |

(*1) % owh: shows mass % of a dye with respect to a mass of hair
(*4) Residual ratio: irradiation 20 Hr (K/Sd)/unirradiation (K/Sd)

From the measurement results of Table 4, even after 20 hours irradiation time by a fade meter, Blue 75 keeps a high dyeing concentration as compared with the other two dyes. In addition, color fastness to light after 20 hours irradiation of Blue 75 is approximately equivalent to that of Blue 99 from the residual ratio thereof, and is considerably excellent as compared with Blue 3.

Example 4

For each test sample obtained in the above described hair dyeing method 1, a shampoo fastness test was carried out in the following conditions. The results thereof are described in Table 5.
(Shampoo Fastness Test Method)
The shampoo fastness test (a shampoo treatment and a conditioner treatment are assumed to be one test, and the test was repeated 5 times) was carried out on each test sample obtained in the above described hair dyeing method 1, followed by drying at room temperature to form a test sample. Then, a dyeing concentration (K/Sd) was measured for the each test sample.
(1) Shampoo Treatment Conditions
Shampoo solution: aqueous 5% lauryl sodium sulfate solution
Bath ratio: 1:10 (mass of a shampoo solution with respect to 1 g of dyeing hair mass)
Temperature, time: 45° C., 20 minutes
Post treatment: washing with water
(2) Conditioner Treatment Conditions
Conditioner solution: aqueous 5% stearyl trimethyl ammonium chloride solution
Bath ratio: 1:10 (mass of a conditioner solution with respect to 1 g of dyeing hair mass)
Temperature, time: 45° C., 20 minutes
Post treatment: washing with water

TABLE 5

| Dye concentration % owh (*1) | Dye name | Dyeing concentration (K/Sd) | | Residual ratio after treatment (%) |
|---|---|---|---|---|
| | | Untreated | Treated (5 times) | |
| 1 | Blue75 | 258 | 124 | 48 |
| | Blue3 | 121 | 47 | 39 |
| | Blue99 | 78 | 18 | 23 |
| 2 | Blue75 | 472 | 275 | 58 |
| | Blue3 | 223 | 124 | 56 |
| | Blue99 | 130 | 41 | 32 |
| 3 | Blue75 | 563 | 306 | 54 |
| | Blue3 | 317 | 128 | 40 |
| | Blue99 | 203 | 57 | 28 |

(*1) % owh: shows mass % of a dye with respect to a mass of hair.

From the measurement results in Table 5, a residual ratio (dyeing concentration) after the shampoo fastness test of Blue 75 is high in any dyeing concentration level, and Blue 75 is excellent in shampoo fastness.

Example 5

In order to know a usable pH of the hair dyeing composition, the pH value is adjusted from 8.5 to around 5, and the dyeing test was carried out.
(Hair Dyeing Method 2)
Dyeing solutions A and C prepared from Blue 75 obtained in Example 1-2 based on composition ratios in Table 2 were weighed in 10 g respectively, and adjusted to pH 5.2 with sodium carbonate, then 1 g of artificial white hair (100%) (product No. BM-W, Beaulax Co., Ltd.) was placed therein, and dyed at 45° C. for 20 minutes. This dyed hair is washed with water and subjected to soaping under the above described soaping conditions and washed with water, and then dried at room temperature to thereby obtain test samples, respectively. Note that when 10 g of these dyeing solutions A and C is used to dye 1 g of hair, dye concentrations respectively correspond to 1% and 3% owh (*1). (% owh (*1): indicates mass % of a dye with respect to a mass of hair.)

Comparative Example 3

Blue 3 was selected as a dye subjected to the test, and treated in accordance with the hair dyeing method 2 in Example 5 to obtain a test sample.

Comparative Example 4

Blue 99 was selected as a dye subjected to the test in the same manner, and treated in accordance with the hair dyeing method 2 in Example 5 to obtain a test sample.

A dyeing concentration of each test sample was measured. The measurement results thereof are described in Table 6.

TABLE 6

| Dye concentration % owh (*1) | Dye name | Dyeing concentration (K/Sd) (*2) | |
|---|---|---|---|
| | | Test sample | Ratio (*3) |
| 1 | Blue75 | 210 | 100 |
| | Blue3 | 82 | (39) |
| | Blue99 | 84 | (40) |
| 3 | Blue75 | 303 | 100 |
| | Blue3 | 125 | (41) |
| | Blue99 | 134 | (44) |

(*1) % owh: shows mass % of a dye with respect to a mass of hair
(*2) K/Sd: value obtained by deducting K/S of undyed hair from K/S of dyeing test sample
(*3) ( ) value: dyeing concentration ratio of each dye when a dyeing concentration of Blue 75 is assumed to be 100

From the measurement results of Table 6, regarding a dyeing concentration of hair at a pH value of 5.2, Blue 75 is high in any concentration level, and is excellent in dyeing properties as compared with Blue 3 and Blue 99. From the measurement results of the above Tables 3 and 6, Blue 75 is capable of being used in a wide pH range, which is thus a dye having excellent dyeing properties.

Example 6

According to the composition contents in Table 2, Blue 75 and Brown 16 were mixed in a predetermined amount shown in Table 7 as a component (a), and a component (b) and a component (c) were blended therein to prepare a brown dye solution, and treated in accordance with the above described hair dyeing method 1. Colorimetry was carried out on each test sample by the colorimeter described below.

The results thereof are described in Table 7.

Device: spectrocolorimeter SE-2000 (manufactured by NIPPON DENSHOKU INDUSTRIES CO., LTD.)
L*a*b color specification system (CIE1976)
Color specification is speculated by the three parameters (L*, a* and b*)
L*, a* and b* indicate chromaticity respectively showing brightness, hue and color saturation.
Larger a L* value is, smaller a strength of coloring is.
a* corresponds to an axis of a pair of red/green. Plus is red, and minus is green.
b* corresponds to an axis of a pair of yellow/blue. Plus is yellow, and minus is blue.

TABLE 7

| Sample No. | Blended dye concentration (% owh) | | L * a * b * (CIE1976) | | |
|---|---|---|---|---|---|
| | Brown16 | Blue75 | L* | a* | b* |
| 1 | 4.25 | 0.75 | 21.27 | −1.49 | 5.13 |
| 2 | 4.50 | 0.50 | 23.94 | 1.21 | 7.94 |
| 3 | 4.75 | 0.25 | 27.04 | 5.34 | 10.45 |
| 4 | 2.25 | 0.25 | 29.75 | 1.57 | 8.75 |
| 5 | 2.375 | 0.125 | 32.66 | 5.92 | 12.08 |

Example 7

According to the composition contents in Table 2, Blue 75, Brown 16 and Red 29 were mixed in a predetermined amount shown in Table 8 as a component (a), and a component (b) and a component (c) were blended therein to prepare a black dye solution, and treated in accordance with the above described hair dyeing method 1. Colorimetry was carried out on each test sample by the colorimeter described above.

The results thereof are described in Table 8.

TABLE 8

| Sample No. | Blended dye concentration (% owh) | | | L * a * b * (CIE1976) | | |
|---|---|---|---|---|---|---|
| | Brown16 | Red29 | Blue75 | L* | a* | b* |
| 6 | 2.0 | 1.0 | 2.0 | 19.40 | −1.84 | −2.24 |
| 7 | 2.1 | 1.25 | 1.65 | 17.56 | −0.74 | −2.01 |

Example 8

According to the composition contents in Table 2, Blue 75, Brown 16 and Red 51 were mixed in a predetermined amount shown in Table 9 as a component (a), and a component (b) and a component (c) were blended therein to prepare a black dye solution, and treated in accordance with the above described hair dyeing method 1. Colorimetry was carried out on each test sample by the colorimeter described above.

The results thereof are described in Table 9.

TABLE 9

| Sample No. | Blended dye concentration (% owh) | | | L * a * b * (CIE1976) | | |
|---|---|---|---|---|---|---|
| | Brown16 | Red51 | Blue75 | L* | a* | b* |
| 8 | 2.4 | 0.7 | 1.9 | 17.83 | −0.22 | −3.64 |
| 9 | 2.25 | 0.75 | 2.0 | 17.93 | −0.08 | −5.34 |

As described in Example 6, Example 7, and Example 8, blending Blue 75, Brown 16 and Red 29, or using Red 51 as an alternative for Red 29 enables to form a black dye preparation. Further, blending Blue 75 and Brown 16 enables to form a brown dye preparation.

Example 9

Regarding the totally four kinds of dye compounds (described in Table 10) of the following dyes (three kinds) used in Example 2, Comparative Example 1 and Comparative Example 2 and the dibutyl product synthesized in Example 1, a stability test of the each dye compound was carried out in the presence of an oxidant, assuming use as an oxidative hair colorant.

TABLE 10

| No. | Dye name |
|---|---|
| (a) | Blue75 |
| (b) | Dibutyl product |
| (c) | Blue3 |
| (d) | Blue99 |

A predetermined amount of a commercially available oxidation cream containing an oxidant was mixed in a color cream (1) containing each dye, and a stability test of a dye with a dye concentration of 0.17% and 0.20% was carried out in the presence of an oxidant (hydrogen peroxide). The blending compositions thereof are described in Tables 11 and 13.

TABLE 11

| | Prescription: | | | |
|---|---|---|---|---|
| | B | | A (Blank) | |
| | Dye concentration: 0.17% | | | |
| | Name: | | | |
| | Color cream (1) | Oxidation cream | Color cream (1) | Xanthan gum (2%) |
| | Composition ratio: | | | |
| Component name: | 4 g | 8 g | 4 g | 8 g |
| Dye | 0.5 | — | 0.5 | — |
| Ethanol | 7.9 | — | 7.9 | — |
| Benzyl alcohol | 26.6 | — | 26.6 | — |
| Water | 63.0 | — | 63.0 | 98 |
| Xanthan gum | 2 | — | 2 | 2 |
| Oxidant ($H_2O_2$) | — | Contained | — | — |
| Total: | 100.0 | 100.0 | 100.0 | 100.0 |

Example 10

Stability Test

In 8 g of a commercially available oxidation cream (two-agent of Mens Bigen Speedy IIN, made by Hoyu Co., Ltd.) containing hydrogen peroxide ($H_2O_2$) as an oxidant, 4 g of a color cream (1) containing 0.5% by mass of the dye, Blue 75, was blended, and stability of the dye compound was tested (prescription B). A dye concentration after the blending was 0.17% by mass. In addition, as a reference (blank), a 2% xanthan gum solution not containing an oxidant was blended in the color cream (1) (prescription A).

Further, since a pH value of the above commercially available oxidation cream was about 4, the xanthan gum solution was adjusted to a pH value of about 4 by adding a citric acid solution (in the measurement of the pH value, a universal litmus paper was used).

(Dyeing Conditions)

To the color cream blended solution prepared in the above described mixing method, 1 g of artificial white hair (100%) (product No. BM-W, Beaulax Co., Ltd.) was placed, and dyed at 45° C. for 20 minutes. This dyed hair was washed with water, subjected to soaping under the above described soaping conditions and washed with water, and then dried at room temperature to thereby obtain each test sample.

(Dyeing Concentration)

A dyeing concentration of each test sample was measured. The result thereof is descried in Table 12.

Example 11

A dibutyl product was selected as a dye, and the dyeing concentration was measured in accordance with the prescription of Example 10. The result thereof is described in Table 12.

Comparative Example 5

Blue 3 was selected for a dye, and the dyeing concentration was measured in accordance with the prescription of Example 10. The result thereof is described in Table 12.

Comparative Example 6

Blue 99 was selected as a dye, and the dyeing concentration was measured in accordance with the prescription of Example 10. The result thereof is described in Table 12.

TABLE 12

| Sample No. | Dye name | Dye concentration (mass %) | Dyeing concentration (K/Sd) (*1) Test sample | Ratio (*2) |
|---|---|---|---|---|
| 1-A | Blue75 | 0.17 | 478 | 100 |
| 1-B | | | 467 | (98) |
| 2-A | Dibutyl product | 0.17 | 454 | 100 |
| 2-B | | | 436 | (96) |
| 3-A | Blue3 | 0.17 | 321 | 100 |
| 3-B | | | 300 | (93) |
| 4-A | Blue99 | 0.17 | 97 | 100 |
| 4-B | | | 76 | (78) |

(*1) K/Sd: value obtained by deducting $K/S_\lambda$ of undyed hair from $K/S_\lambda$ of hair dyeing test sample
(*2) ( ) value: dyeing concentration ratio of B when a dyeing concentration of A is assumed to be 100

TABLE 13

| | Prescription: | | | |
|---|---|---|---|---|
| | B | | A (Blank) | |
| | Dye concentration: 0.20% | | | |
| | Name: | | | |
| | Color cream (2) | Oxidation cream | Color cream (2) | Xanthan gum (2%) |
| | Composition ratio: | | | |
| Component name: | 5 g | 5 g | 5 g | 5 g |
| Dye | 0.4 | — | 0.4 | — |
| Ethanol | 7.9 | — | 7.9 | — |
| Benzyl alcohol | 26.6 | — | 26.6 | — |
| Water | 63.1 | — | 63.1 | 98 |
| Xanthan gum | 2 | — | 2 | 2 |
| Oxidant ($H_2O_2$) | — | Contained | — | — |
| Total: | 100.0 | 100.0 | 100.0 | 100.0 |

Example 12

Stability Test

In 5 g of a commercially available oxidation cream (two-agent of Mens Bigen Speedy IIN, made by Hoyu Co., Ltd.) containing hydrogen peroxide ($H_2O_2$) as an oxidant, 5 g of a color cream (2) containing 0.4% by mass of the dye, Blue 75, was blended, and stability of the dye compound was tested (prescription B). A dye concentration after the blending was 0.20% by mass. In addition, as a reference (blank), a 2% xanthan gum solution not containing an oxidant was blended in the color cream (2) (prescription A).

Further, since a pH value of the above commercially available oxidation cream was about 4, the xanthan gum solution was adjusted to a pH value of about 4 by adding a citric acid solution (in the measurement of the pH value, a universal litmus paper was used).

(Dyeing Conditions)

To the color cream blended solution prepared in the above described mixing method, 1 g of artificial white hair (100%) (product No. BM-W, Beaulax Co., Ltd.) was placed, and dyed at 45° C. for 20 minutes. This dyed hair was washed with water, subjected to soaping under the above described soaping conditions and washed with water, and then dried at room temperature to thereby obtain each test sample.

(Dyeing Concentration)

A dyeing concentration of each test sample was measured. The results thereof are descried in Table 14.

Example 13

A dibutyl product was selected as a dye, and the dyeing concentration was measured in accordance with the prescription of Example 12. The result thereof is described in Table 14.

Comparative Example 7

Blue 3 was selected as a dye, and the dyeing concentration was measured in accordance with the precipitation of Example 12. The result thereof is described in Table 14.

Comparative Example 8

Blue 99 was selected as a dye, and the dyeing concentration was measured in accordance with the prescription of Example 12. The result thereof is described in Table 14.

TABLE 14

| Sample No. | Dye name | Dye concentration (mass %) | Dyeing concentration (K/Sd) (*1) Test sample | Ratio (*2) |
|---|---|---|---|---|
| 5-A | Blue75 | 0.20 | 425 | 100 |
| 5-B | | | 449 | (106) |
| 6-A | Dibutyl product | 0.20 | 418 | 100 |
| 6-B | | | 413 | (99) |
| 7-A | Blue3 | 0.20 | 280 | 100 |
| 7-B | | | 291 | (104) |

TABLE 14-continued

| Sample No. | Dye name | Dye concentration (mass %) | Dyeing concentration (K/Sd) (*1) Test sample | Ratio (*2) |
|---|---|---|---|---|
| 8-A | Blue99 | 0.20 | 132 | 100 |
| 8-B | | | 133 | (101) |

(*1) K/Sd: value obtained by deducting K/S$_\lambda$ of undyed hair from K/S$_\lambda$ of hair dyeing test sample
(*2) ( ) value: dyeing concentration ratio of B when a dyeing concentration of A is assumed to be 100

The stability test of each dye was carried out in the presence of an oxidant (hydrogen peroxide) of the dye assuming use as an oxidative hair colorant. From the results of Table 12 and Table 14, Blue 75 and the dibutyl product have stable dyeing concentrations even in the presence of an oxidant.

Examples 14 to 28 and Comparative Examples 9 to 11

Compositions shown in Table 16 (Comparative Example 9 and Examples 14 to 21), compositions shown in Table 17 (Comparative Example 10 and Example 22), and compositions shown in Table 18 (Comparative Example 11 and Examples 23 to 28) were adjusted to pH 5 with sodium carbonate. These compositions were coated on skin (arm) in a size of about a red bean and left for 5 minutes, then washed with a commercially available soap and washed with water to evaluate by the contamination evaluation method shown in the following Table 15. Results thereof are shown in Tables 16, 17 and 18.

(Contamination Evaluation Method)

Contamination was evaluated by the gray scale for contamination (JIS L0805) with the 9 levels of 5 grade, 4 to 5 grade, 4 grade, 3 to 4 grade, 3 grade, 2 to 3 grade, 2 grade, 1 to 2 grade, and 1 grade. Note that the gray scale for contamination is a standard scale used for determination of a degree of contamination caused on a white fabric in the JIS color fastness test.

The relationship between each grade and a degree of contamination is shown in the following.

TABLE 15

| Grades | Evaluation criteria | Remarks |
|---|---|---|
| 5 grade | Stain in about the 5 grade of the gray scale for contamination | No stain is remained |
| 4 grade | Stain in about the 4 grade of the gray scale for contamination | Almost no stain is remained |
| 3 grade | Stain in about the 3 grade of the gray scale for contamination | Some stains are remained |
| 2 grade | Stain in about the 2 grade of the gray scale for contamination | Stain is considerably remained |
| 1 grade | Stain in the 1 grade or more of the gray scale for contamination | Stain is thickly remained |

TABLE 16

| Compositions | | Comparative Example 9 | Example 14 | Example 15 | Example 16 | Example 17 | Example 18 | Example 19 | Example 20 | Example 21 |
|---|---|---|---|---|---|---|---|---|---|---|
| Blue 75 | Blue75 | 0.2 | 0.2 | 0.2 | 0.2 | 0.2 | 0.2 | 0.2 | 0.2 | 0.2 |
| | Ethanol | 11.0 | 11.0 | 11.0 | 11.0 | 11.0 | 11.0 | 11.0 | 11.0 | 11.0 |
| | Benzyl alcohol | 4.9 | 4.9 | 4.9 | 4.9 | 4.9 | 4.9 | 4.9 | 4.9 | 4.9 |
| | Water | 81.9 | 81.4 | 79.9 | 77.9 | 75.9 | 81.4 | 79.9 | 77.9 | 75.9 |
| | Tween#80 | — | 0.5 | 2.0 | 4.0 | 6.0 | — | — | — | — |

TABLE 16-continued

| Compositions | Comparative Example 9 | Example 14 | Example 15 | Example 16 | Example 17 | Example 18 | Example 19 | Example 20 | Example 21 |
|---|---|---|---|---|---|---|---|---|---|
| Tween#20 | — | — | — | — | — | 0.5 | 2.0 | 4.0 | 6.0 |
| Xanthan gum | 2.0 | 2.0 | 2.0 | 2.0 | 2.0 | 2.0 | 2.0 | 2.0 | 2.0 |
| Total amount (part by weight) | 100 | 100 | 100 | 100 | 100 | 100 | 100 | 100 | 100 |
| Contamination evaluation results | 2-3 | 3-4 | 4 | 4 | 4-5 | 3-4 | 4 | 4 | 4-5 |

Tween#80: polyoxyethylene sorbitan monooleate (made by Kanto Chemical Co., Inc.)
Tween#20: polyoxyethylene sorbitan monolaurate (made by Tokyo Chemical Industry Co., Ltd.)

TABLE 17

| | Compositions | Comparative Example 10 | Example 22 |
|---|---|---|---|
| Blue75 | Blue75 | 0.2 | 0.2 |
| | Ethanol | 9.0 | 9.0 |
| | Benzyl alcohol | 4.0 | 4.0 |
| | Water | 84.3 | 81.3 |
| | Tween#80 | — | 3.0 |
| | Hydroxyethyl cellulose | 2.5 | 2.5 |
| | Total amount (part by weight) | 100 | 100 |
| Contamination evaluation results | | 2 | 4 |

TABLE 18

| | Composition | Comparative Example 11 | Example 23 | Example 24 | Example 25 | Example 26 | Example 27 | Example 28 |
|---|---|---|---|---|---|---|---|---|
| Blending Black | Brown16 | 0.24 | 0.24 | 0.24 | 0.24 | 0.24 | 0.24 | 0.24 |
| | Red51 | 0.07 | 0.07 | 0.07 | 0.07 | 0.07 | 0.07 | 0.07 |
| | Blue75 | 0.19 | 0.19 | 0.19 | 0.19 | 0.19 | 0.19 | 0.19 |
| | Ethanol | 10.9 | 10.9 | 10.9 | 10.9 | 10.9 | 10.9 | 10.9 |
| | Benzyl alcohol | 4.9 | 4.9 | 4.9 | 4.9 | 4.9 | 4.9 | 4.9 |
| | Water | 81.7 | 80.45 | 76.7 | 74.2 | 80.45 | 76.7 | 74.2 |
| | Tween#80 | — | 1.25 | 5.0 | 7.5 | — | — | — |
| | Tween#20 | — | — | — | — | 1.25 | 5.0 | 7.5 |
| | Xanthan gum | 2.0 | 2.0 | 2.0 | 2.0 | 2.0 | 2.0 | 2.0 |
| | Total amount (part by weight) | 100 | 100 | 100 | 100 | 100 | 100 | 100 |
| Contamination evaluation result | | 1 | 2-3 | 4 | 4 | 2-3 | 4 | 4 |

From these test results, since the hair dyeing composition containing the dye of the present invention is excellent in contamination resistance, the hair dyeing composition can be used as a hair colorant composition and an oxidative hair colorant composition, and is considered to be valuable as a blue hair dyeing composition.

INDUSTRIAL APPLICABILITY

When C. I. Basic Blue 75 and its analogue that is a dibutyl product of the present invention dye into keratin fibers of human hair, livestock hair, and the like, they retain high dyeing properties and excellent shampoo fastness. Further, as compared with the case of using conventional cationic dyes, they are excellent dyes remarkably improved in color fastness to light.

The invention claimed is:

1. A hair dye comprising a compound represented by the following general formula (I):

[Chemical Formula 1]

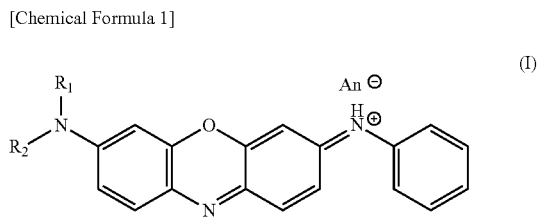

wherein R1 and R2 each independently represent a hydrogen atom or a straight chain or branched alkyl group having 1 to 5 carbon atoms, and An represents an inorganic anion, an organic anion, or a complex salt anion, respectively.

2. The hair dye according to claim 1, wherein the inorganic anion is a chlorine ion, a bromine ion, a sulfate ion, a phosphate ion, or an iodine ion.

3. The hair dye according to claim 1, wherein the complex salt anion is an inorganic complex salt anion represented by the following general formula (II):

$$(ZnCl2)nCl- \quad (II)$$

wherein n represents a number of 0.5 to 1.

4. The hair dye according to claim 1, wherein both $R_1$ and $R_2$ are an ethyl group or an n-butyl group.

5. A hair dyeing composition, comprising the hair dye according to claim 1, at least one auxiliary agent selected from the group consisting of a wetting agent, a swelling agent, a penetrant, a pH regulator, a surfactant, a perfume and a thickener, and water.

6. The hair dyeing composition according to claim 5, further comprising an oxidative dye, an alkaline agent, and an oxidant.

7. The hair dyeing composition according to claim 5, wherein a content of the hair dye is 0.001 to 5% by mass on the basis of the total amount.

8. The hair dyeing composition according to claim 5, wherein a pH is 3 to 10.

9. The hair dyeing composition according to claim 5, wherein the surfactant is a polyoxyethylene sorbitan fatty acid ester.

10. The hair dyeing composition according to claim 9, wherein the polyoxyethylene sorbitan fatty acid ester is at least one selected from the group consisting of polyoxyethylene sorbitan monolaurate, polyoxyethylene sorbitan monopalmitate, polyoxyethylene sorbitan monosterate and polyoxyethylene sorbitan monooleate.

11. The hair dyeing composition according to claim 9, wherein a content of the polyoxyethylene sorbitan fatty acid ester is 2.5 to 30 fold more than the amount of the hair dye on the mass basis.

12. A compound represented by the following general formula (Ia):

[Chemical Formula 2]

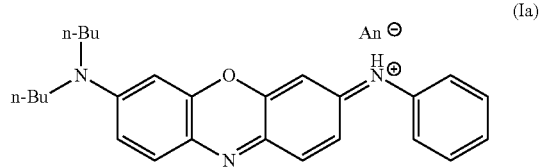

(Ia)

wherein An– represents an inorganic anion, an organic anion, or a complex salt anion.

13. The compound according to claim 12, wherein the inorganic anion is a chlorine ion, a bromine ion, a sulfate ion, a phosphate ion, or an iodine ion.

14. The compound according to claim 12, wherein the complex salt anion is an inorganic complex salt anion represented by the following general formula (II):

$(ZnCl2)nCl-$ (II)

wherein n represents a number of 0.5 to 1.

* * * * *